US008507548B2

(12) United States Patent
Lines

(10) Patent No.: US 8,507,548 B2
(45) Date of Patent: *Aug. 13, 2013

(54) METHOD FOR TREATING ADDICTION USING QUERCETIN-CONTAINING COMPOSITIONS

(75) Inventor: Thomas Christian Lines, Wayland, MA (US)

(73) Assignee: Quercegen Pharmaceuticals LLC, Marlborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/215,629

(22) Filed: Aug. 23, 2011

(65) Prior Publication Data
US 2012/0053137 A1 Mar. 1, 2012

Related U.S. Application Data

(63) Continuation of application No. 12/355,208, filed on Jan. 16, 2009, now Pat. No. 8,044,096.

(60) Provisional application No. 61/021,937, filed on Jan. 18, 2008.

(51) Int. Cl.
A61K 31/352 (2006.01)
A61K 31/375 (2006.01)
A61K 31/445 (2006.01)

(52) U.S. Cl.
USPC ............................ 514/456; 514/355; 514/356

(58) Field of Classification Search
USPC .................................. 514/456, 27, 355, 356
See application file for complete search history.

(56) References Cited

U.S. PATENT DOCUMENTS

| | | | |
|---|---|---|---|
| 5,026,721 A | 6/1991 | Dudrick et al. | |
| 5,308,627 A * | 5/1994 | Umbdenstock, Jr. | 424/639 |
| 5,804,594 A | 9/1998 | Murad | |
| 5,846,569 A | 12/1998 | Anderson et al. | |
| 6,103,756 A | 8/2000 | Gorsek | |
| 6,203,818 B1 | 3/2001 | Vester | |
| 6,210,701 B1 | 4/2001 | Darland et al. | |
| 6,261,589 B1 | 7/2001 | Pearson et al. | |
| 6,277,426 B1 | 8/2001 | Reust | |
| 6,277,427 B1 | 8/2001 | Husz | |
| 6,299,925 B1 | 10/2001 | Xiong et al. | |
| 6,352,712 B1 | 3/2002 | Lukaczer et al. | |
| 6,491,948 B1 | 12/2002 | Buchholz et al. | |
| 6,511,675 B2 | 1/2003 | Siddiqui et al. | |
| 6,551,629 B1 | 4/2003 | Gorsek | |
| 6,579,544 B1 | 6/2003 | Rosenberg et al. | |
| 6,821,536 B2 | 11/2004 | Lines et al. | |
| 7,041,652 B1 | 5/2006 | Buchholz et al. | |
| 7,049,301 B2 * | 5/2006 | Zhao et al. | 514/27 |
| 7,270,840 B2 | 9/2007 | Lines et al. | |
| 2002/0025350 A1 | 2/2002 | Siddiqui et al. | |
| 2002/0151599 A1 | 10/2002 | Buchholz et al. | |
| 2003/0054357 A1 | 3/2003 | Young et al. | |
| 2003/0068391 A1 | 4/2003 | Harris et al. | |
| 2004/0126461 A1 | 7/2004 | Lines et al. | |
| 2005/0031737 A1 | 2/2005 | Lines et al. | |
| 2005/0266121 A1 | 12/2005 | Lines et al. | |
| 2006/0204601 A1 | 9/2006 | Palu et al. | |
| 2007/0148210 A1 | 6/2007 | Lines et al. | |

FOREIGN PATENT DOCUMENTS

| | | |
|---|---|---|
| WO | WO95-29668 | 11/1995 |
| WO | WO 98/41195 | 9/1998 |
| WO | WO 00/12085 | 3/2000 |
| WO | WO 02/07768 | 1/2002 |
| WO | WO 2008/011364 | 1/2008 |

OTHER PUBLICATIONS

Habibi et al 2007; The effect of quercetin and ACTH on morphine-induced tolerance and dependence in mice. Ulm-i Daroei (2007) (1), 1-9 ISSN: 1735-403X.*
Bors et al., "Flavanoids and Polyphenols: Chemistry and Biology," Handbook of Antioxidants, pp. 409-416 (1996).
Chow et al., "Phase I Pharmacokinetic Study of Tea Polyphenols Following Single-dose Administration of Epigallocatechin Gallate and Polyphenon E," Cancer Epidemiology, Biomarkers & Prevention 10:53-58 (2001) XP-002366662.
Crespy et al., "Quercetin, but not Its Glycosides, Is Absorbed from the Rat Stomach," Journal of Agricultural and Food Chemistry, vol. 50, pp. 68-621 (2002).
Dequan et al., "Survey of Bioflavonoids," Food and Fermentation Industries, 25(16): 52-56 (1999) (Translation of English Abstract).
Erlund et al., "Pharmacokinetics of Quercetin from Quercetin Aglycone and Rutin in Healthy Volunteers," Eur. J. Clin. Pharmacol., 56:545-553 (2000).
Guardia et al., "Anti-Inflammatory Properties of Plant Flavinoids. Effect of Rutin, Quercetin and Hesperidin on Adjuvant Arthritis in Rat," Il Farmaco, 56: 683-687 (2001).
Koo et al., "Pharmacological Effects of Green Tea on the Gastrointestinal System," European Journal of Pharmacology 500:177-184 (2004).
Min et al., "The Chemistry and Medical Application of Tea Polyphenol," Hubei Chemical Industry, 2001, 3, 29-31 (Translation of English Abstract).
Saucier et al., "Synergetic Activity of Catechin and Other Antioxidants," Journal of Agricultural and Food Chemistry, 47(11): 4491-4494 (1999).
Sesink et al., "Quercetin Glucuronides but Not Glucosides Are Present in Human Plasma After Consumption of Quercetin-3-Glucoside or Quercetin-4-Glucoside," Human Nutrition and Metabolism Research Communication, pp. 1938-1941 (2001).
Thomas et al., "Ascorbate and Phenolic Antioxidant Interations in Prevention of Liposomal Oxidation," Lipids 27(7) (1992).
Walle et al., "Quercetin Glucosides Are Completely Hydrolyzed in Ileostomy Patients before Absorption," Human Nutrition and Metabolism Research Communication, pp. 2658-2661 (2000).

(Continued)

Primary Examiner — Jennifer M Kim
(74) Attorney, Agent, or Firm — Occhiuti Rohlicek & Tsao LLP

(57) ABSTRACT

This invention relates to a method of treating addiction using a composition containing quercetin. Preferably, it also contains vitamin $B_3$, and vitamin C.

18 Claims, No Drawings

(56) References Cited

OTHER PUBLICATIONS

Singh et al., "Quercetin, a Bioflavonoid, Reverses Development of Tolerance and Dependence to Morphine", Drug Development Research, 2002, vol. 57, pp. 167-172.

Pan et al. "Oxidative stree in heroin administered mice and natural antioxidants protection." Life Sciences, Pergamon Press, Oxford, GB, vol. 77, No. 2, May 27, 2005, pp. 183-193.

* cited by examiner

METHOD FOR TREATING ADDICTION USING QUERCETIN-CONTAINING COMPOSITIONS

CROSS-REFERENCE TO RELATED APPLICATIONS

This application is a continuation of U.S. application Ser. No. 12/355,208 filed Jan. 16, 2009, which claims the benefit of U.S. Provisional Application No. 61/021,937 filed Jan. 18, 2008. The contents of both prior applications are incorporated herewith in their entirety.

BACKGROUND

Quercetin, a natural antioxidant, is known to inhibit both acute and chronic phases of free-radical induced diseases. It has also been found to alleviate withdrawal symptoms accompanied with addiction, e.g., alcohol abstinence-induced anxiety and convulsion. See Joshi et al., J. Med. Food., 8(3):392-396 (2005).

SUMMARY

The present invention features a method for treating addiction by administering to a subject in need thereof (e.g., a person addicted to a substance, such as alcohol, nicotine, or abusive drug), an effective amount of a quercetin-containing composition, which preferably also includes vitamin $B_3$ and vitamin C. In one example, the composition contains quercetin, vitamin $B_3$, and vitamin C at a weight ratio of 1:0.02-1:0.2-2.5.

The composition used in the above-described treatment, either in dry form (e.g., powder or tablet) or in liquid form (e.g., beverage or syrup), can be a dietary supplement or a pharmaceutical formulation, both of which can be in the form of a tablet, a capsule, a soft chew, or a gel. The composition can also be a food product, including tea (e.g., a tea drink and the contents of a tea bag), soft drink, juice (e.g., a fruit extract and a juice drink), milk, coffee, jelly, ice cream, yogurt, cookie, cereal, chocolate, and snack bar.

The details of one or more embodiments of the invention are set forth in the description below. Other features, objects, and advantages of the invention will be apparent from the description and from the claims.

DETAILED DESCRIPTION

This invention aims at using a quercetin-containing composition for treating addiction. Preferably, this composition also includes vitamin $B_3$ and vitamin C.

Addiction refers to a person's engagement, under recurring compulsion, in a certain activity, e.g., drinking, smoking, chewing tobacco, gambling, shopping, or overeating. That person is either addicted to the activity per se (e.g., gambling) or to a substance taken during the activity (e.g., nicotine taken in smoking or chewing tobacco). Substances that cause addiction include, but are not limited to, alcohol, nicotine, heroine, opiate, methamphetamine, cannabinoid, cocaine, bartiturate, hallucinogen (e.g., tryptamine, phencyclidine, psilocybin, or lysergic acid diethylamide), benzodiazepine, and marijuana. When an activity or intake of a substance is suddenly discontinued, a person addicted to the activity/substance would exhibit so-called withdrawal symptoms, such as physical discomfort, irritability, insomnia, depression, or anorexia. It has been found that neurotransmitters, e.g., dopamine and norepinephrine, play an important role in addiction. For example, the euphoric effects of drugs are thought to be a direct result of drug-induced acute increase of dopamine in brain.

Without being bound by theory, quercetin may function as an anti-addiction agent via the following mechanism. Quercetin has been found to block re-uptake of neurotransmitters by neuron cells. As a result, it helps maintain increased levels of neurotransmitters induced by an addictive substance (e.g., an abusive drug), and in turn, euphoric effects caused by the substance. In other words, quercetin reduces the amount of the substance that an addict needs for experiencing the euphoric effects, thus assisting withdrawal from addiction to the substance. Quercetin's anti-addiction efficacy is enhanced by vitamin $B_3$ and vitamin C. More specifically, concurrent administration of quercetin, vitamin $B_3$, and vitamin C results in a significantly higher quercetin concentration in plasma than quercetin alone. The half-life of quercetin is twice as long as that of quercetin alone.

A composition containing quercetin, vitamin $B_3$, and vitamin C has also been found to lead to increased mitochondrial biogenesis or retention (e.g., in muscle and brain cells), reduced mitochondrial DNA damage/loss of mitochondria, or increased cytochrome C levels/citrate synthase activities. Thus, this composition is useful in treating diseases or disorders associated with mitochondrial deficiencies, e.g., depression (a withdrawal symptom of addiction).

Accordingly, the present invention features use of a composition containing quercetin, or, preferably also containing vitamin $B_3$ and vitamin C, for treating addiction. The term "quercetin" refers to both quercetin aglycon and quercetin derivatives, e.g., quercetin-3-O-glucoside, quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, which are absorbed in the body. The term "treating" refers to the administration of an effective amount of a quercetin-containing composition to a subject addicted to either an activity or a substance with the purpose to reduce the subject's dependence to the activity/substance, or to improve one or more of the conditions/symptoms accompanied with addicting to or withdrawal from the activity/substance, or to prevent, cure, alleviate, relieve, remedy, or ameliorate one or more of the conditions/symptoms, or the predispositions of one or more of them.

An example of a composition for practicing this invention includes quercetin, vitamin $B_3$, and vitamin C, the weight ratio of which in the composition can be 1:0.02-1:0.2-2.5, or any ratio in between. For example, the weight ratio can be 1:0.04-0.5:0.3-2.0, 1:0.05-0.3:0.4-1.5, 1:0.05-0.2:0.5-1, and 1:0.1-0.2:0.5-1. Preferred ratios include about 1:0.02:1, about 1:0.04:1, about 1:0.08:1, about 1:0.05:1.5, and about 1:0.16:1.

Typically, a subject can be administered, once or periodically per day, with an effective amount of the composition, e.g., in an amount that provides 100 mg to 2 g (preferably, 250 mg to 1 g) of quercetin. The quantity of quercetin mentioned above refers to that of quercetin aglycon or the quercetin moiety of a quercetin derivative. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil). "Vitamin $B_3$" mentioned herein includes vitamin $B_3$ in its various forms, including niacinamide, nicotinic acid, nicotinamide, inositol hexaniacinate. "Vitamin C" mentioned herein includes vitamin C (i.e., L-ascorbic acid, D-ascorbic acid, or both) and its salts (e.g., sodium ascorbate).

The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. An "effective amount" refers to a dose of the composition that is sufficient to provide a physical benefit (e.g., improving endurance) or a therapeutic benefit (e.g., reducing dependency to an addictive substance, or improving a symptom associated with addiction or withdrawal from addiction). Both in vivo and in vitro studies can be conducted to determine optimal administration routes and doses.

The composition used in the method of this invention can be in various forms. For example, it can be a soft chew composition that includes quercetin, niacinamide, ascorbic acid, sodium ascorbate, sugar, corn syrup, sucralose, soy lecithin, corn starch, clycerin, palm oil, xylitol, carrageenan, FD&C Yellow #6, FD&C Yellow #5, and natural and/or artificial flavors. An exemplary serving of this soft chew composition (5.15 g) includes 250 mg of quercetin, 12.9 mg of vitamin $B_3$ (i.e., niacinamide), and 382.8 mg vitamin C (i.e., L-ascorbic acid and sodium ascorbate). A subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of quercetin, 0.25 wt % of vitamin B3, and 7.81 wt % of vitamin C (i.e., L-ascorbic acid and sodium ascorbate).

The composition can further contain one or more of active ingredients, such as an isoflavone (e.g., genistein or genistin), curcumin, resveratrol, isoquercetin, luteolin, epigallocatechin gallate (EGCG), CoQ10, eicosapentaenoic acid (EPA), and docosahexaenoic acid (DHA). These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose. The composition can also contain amino acids, fatty acids, proteins, fibers, minerals, a flavor enhancer, or a coloring agent. Exemplary amino acids include theanine (e.g., L-theanine) and alanine (e.g., L-alanine). Exemplary fatty acids include omega-3 fatty acids (e.g., linolenic acid), omega-6 fatty acids (e.g., linoleic acid), and omega-9 fatty acids (e.g., oleic acid). Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The composition of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

The compositions described above can be preliminarily screened for their efficacy in treating the above-described conditions in animal models and in clinic trials. Other suitable analytical and biological assays are apparent to those of ordinary skill in the art. For example, the bioavailability of quercetin can be measured by conducting pharmacokinetic studies and evaluated by the area under the curve in a plasma-drug concentration time curve.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating addiction, comprising administering to a subject in need thereof an effective amount of a composition containing quercetin, vitamin $B_3$, and vitamin C, wherein the composition contains quercetin, vitamin $B_3$, and vitamin C at a weight ratio of 1:0.02-1:0.2-2.5.

2. The method of claim 1, wherein the weight ratio is 1:0.1-0.2:0.5-1.

3. The method of claim 1, wherein the weight ratio is 1:0.08:1.

4. The method of claim 1, wherein the composition is in dry form.

5. The method of claim 1, wherein the composition is in liquid form.

6. The method of claim 1, wherein the composition is a food product.

7. The method of claim 6, wherein the food is tea, soft drink, juice, milk, coffee, jelly, ice cream, yogurt, cookie, cereal, chocolate, or snack bar.

8. The method of claim 1, wherein the composition is a dietary supplement or a pharmaceutical formulation.

9. The method of claim 8, wherein the composition is a tablet, a capsule, a soft chew, or a gel.

10. The method of claim 1, wherein the subject is addicted to a substance.

11. The method of claim 10, wherein the substance is alcohol or a drug of abuse.

12. The method of claim 11, wherein the substance is a drug of abuse.

13. The method of claim 12, wherein the weight ratio is 1:0.08:1.

14. The method of claim 12, wherein the composition is a food product.

15. The method of claim 14, wherein the food is tea, soft drink, juice, milk, coffee, jelly, ice cream, yogurt, cookie, cereal, chocolate, or snack bar.

16. The method of claim 12, wherein the composition is a dietary supplement or a pharmaceutical formulation.

17. The method of claim 16, wherein the composition is a tablet, a capsule, a soft chew, or a gel.

18. The method of claim 12, wherein the drug of abuse is selected from the group consisting of opiate, methamphetamine, cannabinoid, cocaine, benzodiazepine, barbiturate, hallucinogen, marijuana, and heroin.

* * * * *